Sept. 5, 1950 P. J. BURGOYNE Plant Pat. 979
IVY PLANT
Filed Sept. 8, 1949
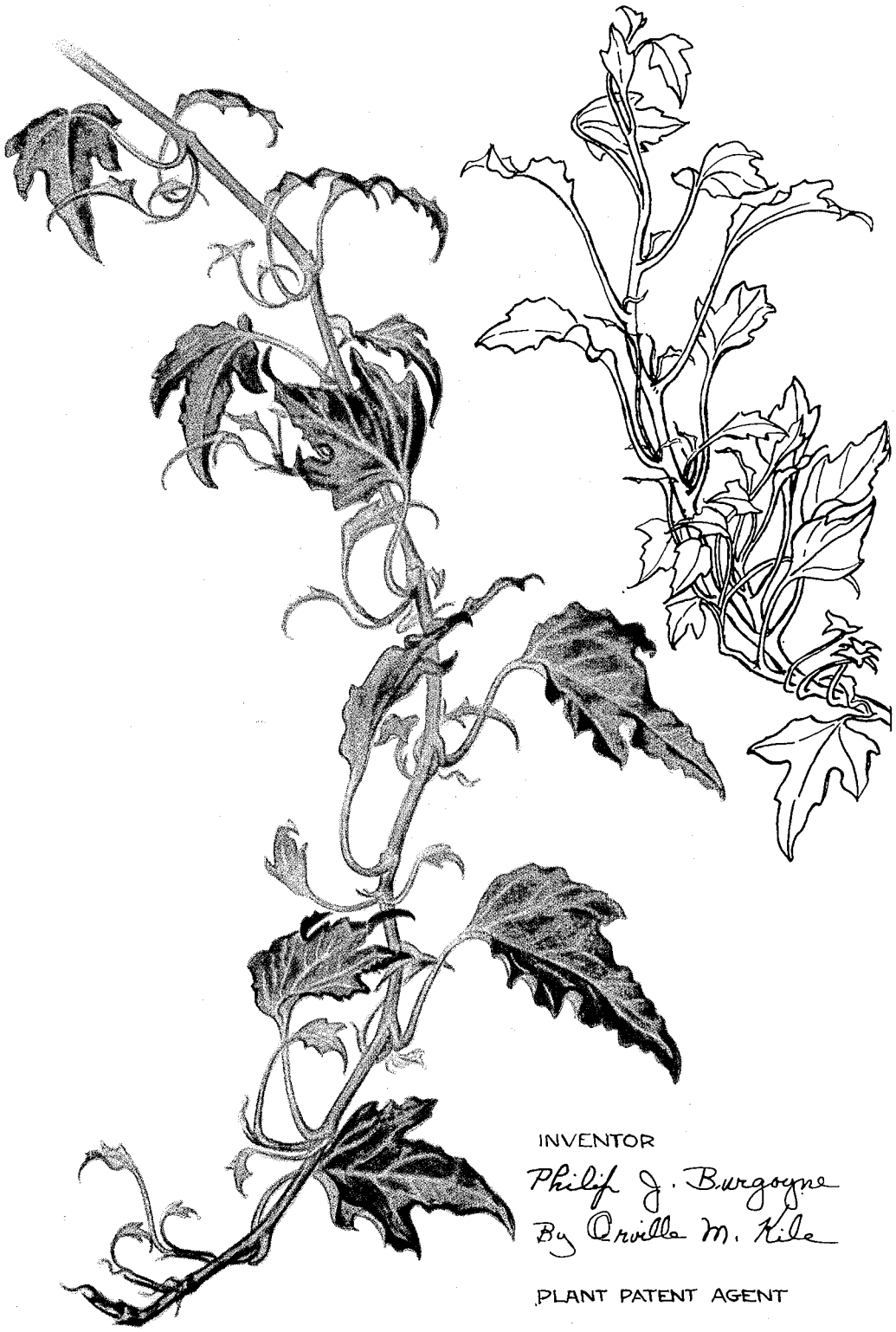
INVENTOR
Philip J. Burgoyne
By Orville M. Kile
PLANT PATENT AGENT Patented Sept. 5, 1950

Plant Pat. 979

UNITED STATES PATENT OFFICE

979

IVY PLANT

Philip J. Burgoyne, Georgetown, Ill.

Application September 8, 1949, Serial No. 114,517

1 Claim. (Cl. 47—59)

My present discovery relates to a new and distinct variety of ivy plant, which originated as a sport from Hahn's self-branching ivy in my gardens at Georgetown, Illinois. I have reproduced it from cuttings in the same gardens, and its characteristics have proved to be permanent.

The accompanying illustrations show (in approximately true colors but enlarged in the original) a branch of my new variety of ivy as extending downward from a hanging basket and allowed to lengthen without pinching. At the right is an outline sketch of a branch of a small plant which has been pinched back and has become very compact in growth.

In the following description, color plate references indicate Ridgway's Color Standards and Nomenclature, and where no plate reference is given the ordinary dictionary meaning is intended.

Probably the most outstanding feature of this new variety of ivy is its lacy and dainty appearance, this being the result of a combination of several of its novel characteristics. The leaves are small and much longer in proportion to their width than is true of any other ivy known to me, and this makes much narrower and daintier leaves. The plant is freely self-branching and produces without pinching, at nearly every node of the stem, new shoots consisting of several small, lighter-colored, delicately fine leaves. With very little pinching a very compact plant is produced, and the variety is extremely easy to propagate in ordinary media, multiplying rapidly because of its very free self-branching habit.

The stems are purplish or bronzed, slender, finely pubescent, and very graceful when allowed to lengthen. The internodes of the stem are short, bringing the leaves rather close together even on the new stems. The stems, together with the dark green of the older leaves and the lighter green of the new leaves produces an unusual and striking effect in color contrast.

The leaf is definitely smaller than on most ivies, becoming only about 2¼ inches long and 1¼ inches wide at the widest point. The leaves are usually three-lobed but a few of the larger and older ones are five-lobed. The terminal lobe is typically lanceolate and its length three or four times its width, although a few of the leaves do not have as great proportionate length as this. Lateral lobes are much shorter than the terminal lobe and extend not more than one-third the length of the terminal lobe. This makes a very long and narrow leaf with acute apex. Basal lobes of the five-lobed leaves are much smaller than the lateral lobes. They are not deeply cut and are really little more than notches. Petioles are long in proportion to lobes of the leaf, being approximately an inch long which is almost as long as the internodes of the stem.

The older leaves are more nearly Empire Green (Plate XXXII) than any other color shown in Ridgway's, and the veins which are slightly raised are much lighter, being approximately Bice Green (Plate XVII). The under surface of the leaf is uniformly Cress Green (Plate XXXI). The small, new leaves are much lighter in color, the under surface being approximately Parrot Green (Plate VI) and the upper surface between that color and Spinach Green (Plate V).

Having thus disclosed my invention, I claim:

The new and improved variety of ivy plant, substantially as herein shown and described, characterized particularly by its very strong self-branching habit; its compact growth with little pinching; its ease of propagation; its slender and graceful purplish or bronzed stems; its long and narrow small leaves with lanceolate central lobe; the dark green of the older leaves with lighter green, slightly raised veins; the dainty and lacy appearance of the plant produced particularly by the narrow leaves and the small new leaves of lighter green color which appear at nearly every node on the stem.

PHILIP J. BURGOYNE.

No references cited.